United States Patent
Koo et al.

(10) Patent No.: US 7,470,822 B2
(45) Date of Patent: Dec. 30, 2008

(54) C10 DIALDEHYDE, SYNTHETIC METHOD THEREOF, AND SYNTHETIC METHOD OF BETA-CAROTENE USING THE SAME

(75) Inventors: Sangho Koo, Seoul (KR); Samar Kumar Guha, Kunggi-Do (KR)

(73) Assignee: Myongji University Industry and Academia Cooperation (KR)

( * ) Notice: Subject to any disclaimer, the term of this patent is extended or adjusted under 35 U.S.C. 154(b) by 0 days.

(21) Appl. No.: 11/576,580

(22) PCT Filed: Jul. 15, 2005

(86) PCT No.: PCT/KR2005/002273

§ 371 (c)(1),
(2), (4) Date: Aug. 10, 2007

(87) PCT Pub. No.: WO2006/038764

PCT Pub. Date: Apr. 13, 2006

(65) Prior Publication Data

US 2008/0262271 A1  Oct. 23, 2008

(30) Foreign Application Priority Data

Oct. 5, 2004  (KR) ...................... 10-2004-0078975

(51) Int. Cl.
*C07C 45/00* (2006.01)
*C07C 47/21* (2006.01)
*C07C 403/00* (2006.01)

(52) U.S. Cl. ........................ 568/449; 568/494; 585/351

(58) Field of Classification Search ................. 568/449, 568/494; 585/351
See application file for complete search history.

(56) References Cited

U.S. PATENT DOCUMENTS

| 4,883,887 A | 11/1989 | Bernhard et al. |
| 5,185,486 A | 2/1993 | Collin et al. |
| 5,276,209 A | 1/1994 | Jaedicke et al. |
| 6,297,416 B1 | 10/2001 | Koo et al. |

FOREIGN PATENT DOCUMENTS

EP  0523534  1/1993

OTHER PUBLICATIONS

International Search Report for PCT/KR2005/002273.

*Primary Examiner*—Sikarl A Witherspoon
(74) *Attorney, Agent, or Firm*—Heslin Rothenberg Farley & Mesiti P.C.

(57) ABSTRACT

The novel intermediate compound which can be efficiently utilized in the synthesis of carotenoid compounds based on the sulfone chemistry, the preparation method of the same, and the practical synthetic process for preparing β-carotene by the use of the above novel compound are disclosed. The synthesis of β-carotene is characterized by the double elimination reactions of the $C_{40}$ compound containing both the benzenesulfonyl group and the group X (either halogen or ether), which can be prepared by the coupling reaction of the novel $C_{10}$ dialdehyde with two equivalents of the $C_{15}$ allylic sulfone, followed by the functional group transformation of the resulting $C_{40}$ diol either to the corresponding halide or to the ether, to produce the fully conjugated polyene chain.

8 Claims, No Drawings

C10 DIALDEHYDE, SYNTHETIC METHOD THEREOF, AND SYNTHETIC METHOD OF BETA-CAROTENE USING THE SAME

CROSS REFERENCE TO RELATED APPLICATIONS

This application is a 35 U.S.C. § 371 U.S. national stage filing from PCT Application Ser. No. PCT/KR2005/002273, having an international filing date of Jul. 15, 2005 published in English on Apr. 13, 2006 under Publication No. WO2006/038764, which claims priority from Application Ser. No. 10-2004-0078975, filed Oct. 5, 2004, which are hereby incorporated by reference in their entirety.

TECHNICAL FIELD

The present invention relates to a novel C10 dialdehyde, synthetic method thereof, and synthetic method of β-carotene using the same. More specifically, it relates to the novel compound, 2,7-dimethyl-4-octenedial, which can be efficiently utilized in the synthesis of carotenoid compounds containing the conjugated polyene chains, a process for preparing the same, and a process for the practical synthesis of β-carotene by using the above novel compound.

BACKGROUND ART

Carotenoid compounds are characterized by the conjugated polyene chains, and some of the representative examples are β-carotene, lycopene, and astaxanthin etc. β-Carotene have found not only the industrial applications as animal feeds and colorants for foodstuffs but also the medicinal applications due to its prophylaxis effects on certain cancers by selectively reacting with cancer suspects such as singlet oxygen and radicals. Therefore, β-carotene has been widely utilized as food additives and nutraceuticals.

One of the representative synthetic methods of β-carotene is delineated in Scheme 1, which has been the commercial process of Hoffmann-La Roche (Isler, O; Lindlar, H.; Montavon, M.; Ruegg, R.; Zeller, P. *Helv. Chim. Acta* 1956, 39, 249-259). The key of the process is the coupling reaction of two moles of the $C_{19}$ units with one mole of bis-magnesium acetylide. Partial hydrogenation of the coupled $C_{40}$ diol, followed by dehydration under an acidic condition then produced β-carotene. According to the above Roche process, it required two consecutive condensation reactions with enol ethers to prepare the $C_{19}$ unit from the $C_{14}$ aldehyde. The above non-convergent and length steps, not to mention of the stereochemical issue of the polyene chain, made the process less practical.

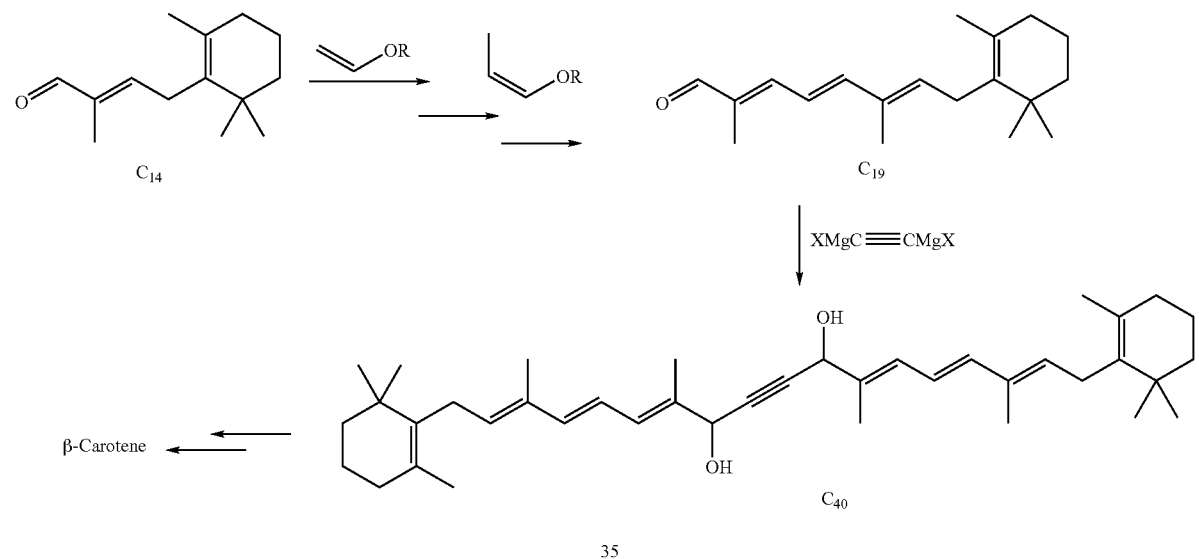

Scheme 1

The second representative synthetic method of β-carotene, which was adopted by BASF as a commercial route, is described in Scheme 2, in which the Wittig reaction of two moles of the $C_{15}$ phosphonium salt and one mole of the $C_{10}$ dialdehyde produced β-carotene (Wittig, G.; Pommer, H. German Patent 954,247, 1956). This process was composed of short reaction steps, and efficiently formed the conjugated polyene chain by the Wittig reaction. However, there is a major problem in the purification of β-carotene from phosphine oxide ($Ph_3P=O$), the byproduct of the Wittig reaction.

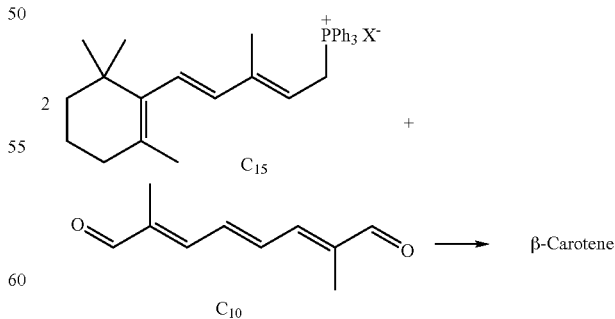

Scheme 2

To overcome the afore-mentioned problems, we recently developed the practical synthetic method of β-carotene, which was composed of relatively short steps and had a strong advantage in the purification of β-carotene from a byproduct in the formation of the conjugated polyene chain (Koo, S.; Choi, H.; Ji, M.; Park, M. WO 00/27810; Koo, S.; Yang, J.-D.; Kim, J.-S.; Lee, S.; Park M. WO 03/037,854). This process utilized the Julia coupling reaction of two moles of the $C_{15}$ allylic sulfone compound and one mole of the $C_{10}$ dihalide compound to construct the required $C_{40}$ carbon skeleton. The Ramberg-Bäcklund reaction of the central allylic sulfone moiety to give the conjugated triene, followed by dehydrosulfonylation reactions produced β-carotene containing the fully conjugated polyene chain (Scheme 3).

the present invention is to provide an improved synthetic process for preparing β-carotene (Chemical Formula 2) with practical and economical values by employing the above novel $C_{10}$ dialdehyde.

Technical Solution

The first technical object of the present invention is achieved by the novel $C_{10}$ dialdehyde, 2,7-dimethyl-4-octenedial, represented by the Chemical Formula 1.

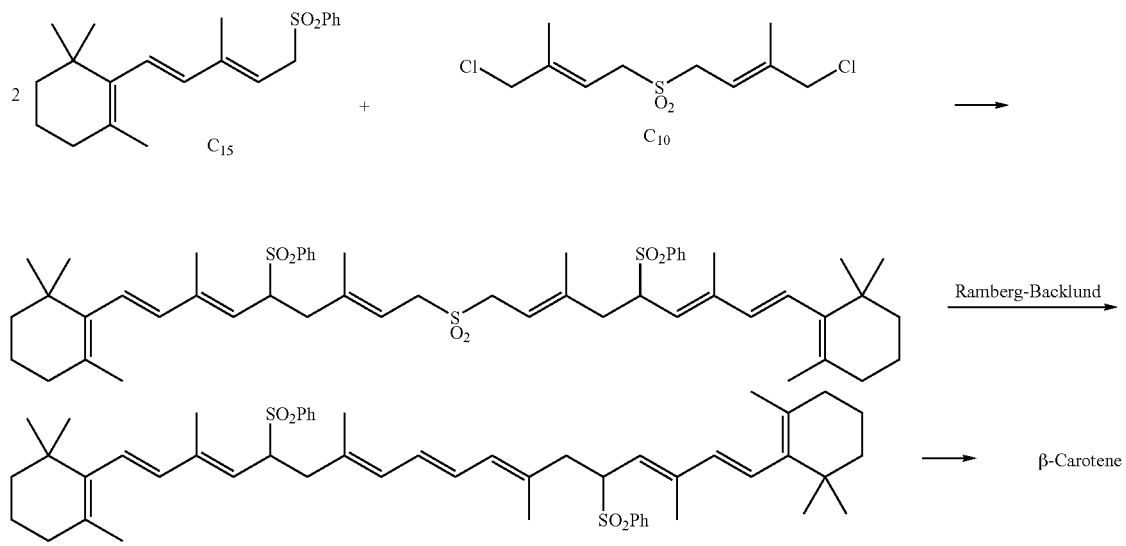

Scheme 3

The above sulfone-mediated process for β-carotene has several advantages over the other methods. The stable intermediates are formed through the process, which can be easily purified by recrystallization. Biologically more active all-(E)-β-carotene can be produced stereoselectively in the dehydrosulfonylation process. However, there is a crucial disadvantage in the above process. The formation of the central conjugated triene unit of E-configuration by the Ramberg-Bäcklund reaction was not a trivial transformation, which gave less than 70% yield of the desired product with a significant amount of the (Z)-isomer. It was thus instantly requested to devise a better synthetic method of β-carotene with practical and economical values based on the Julia sulfone-mediated coupling and olefination protocol not going through the Ramberg-Bäcklund reaction to overcome the above disadvantage.

DISCLOSURE OF INVENTION

Technical Problem

In order to fulfill the above request, we devised a novel compound and the efficient synthetic method of β-carotene utilizing the above novel compound without going through the Ramberg-Bäcklund reaction, which are described in the present invention. Thus, the technical object of the present invention is to provide a novel $C_{10}$ dialdehyde (Chemical Formula 1) and the preparation method of the same in order to overcome the disadvantages in the preparation of the central conjugated triene unit by the Ramberg-Bäcklund reaction based on the sulfone chemistry. Another technical object of Chemical Formula 1

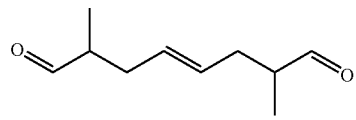

The second technical object of the present invention is achieved by a process for preparing the above novel $C_{10}$ dialdehyde which comprises the steps of:

(a-1) reacting 1,3-butadiene with bromine to give (E)-1,4-dibromo-2-butene (A);

(b-1) reacting the above compound (A) with dialkyl methylmalonate to produce 2,7-dialkoxycarbonyl-2,7-dimethyl-4-octenedioic acid, dialkyl ester (B);

(c-1) hydrolyzing the above tetraester (B) to produce tetraacid, followed by decarboxylating the tetraacid to give the diacid, and then reacting the diacid with alcohols containing carbon numbers of less than ten to provide 2,7-dimethyl-4-octenedioic acid, dialkyl ester (C);

(d-1) reducing the diester (C) to give 2,7-dimethyl-4-octene-1,8-diol (D); and (e-1) oxidizing the above diol (D) to 2,7-dimethyl-4-octenedial, represented by the Chemical Formula 1 (see Scheme 4).

Scheme 4

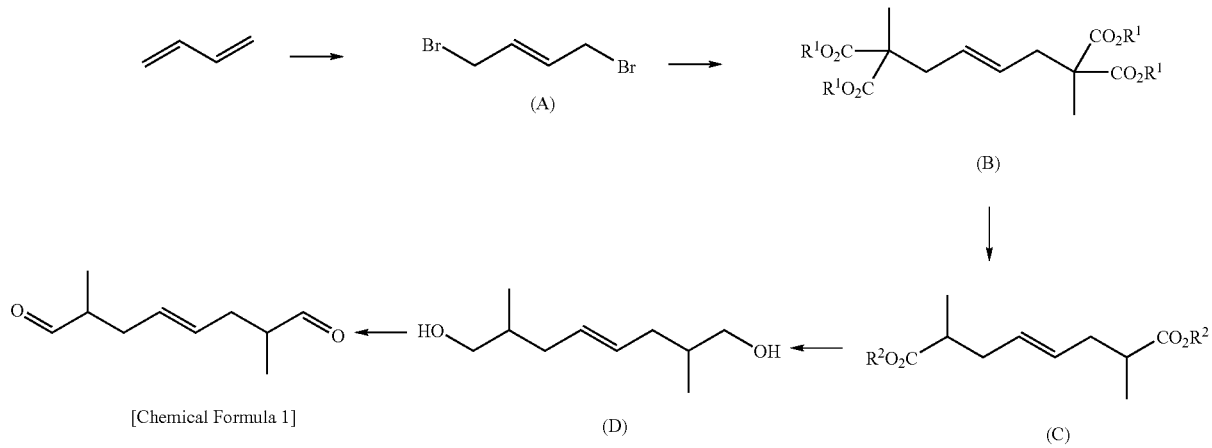

In the above formulas, $R^1$ and $R^2$ are independently selected from the alkyl groups containing carbon numbers of less than ten.

In the above step (a-1), the bromination reaction of 1,3-butadiene is preferably carried out at temperatures below −20° C. The desired (E)-1,4-dibromo-2-butene (A) can be easily purified by recrystallization from non-poplar solvents such as hexanes to remove the side product, 1,2-dibromo-3-butene.

In the above step (b-1), the deprotonation of methylmalonate can be carried out by a base such as NaH or metal alkoxides in THF or the corresponding alcohol solvents of the metal alkoxides.

In the above step (c-1), it is preferable to carry out the sequence of removing two ester groups from the compound (B) containing four ester groups as the following procedure: hydrolyzing the ester groups of the compound (B) under an alkaline condition such as NaOH or KOH solution at reflux temperatures to produce the tetraacid compound, adding concentrated sulfuric acid or nitric acid to adjust the pH of the solution to ~1, refluxing the mixture for decarboxylation to give diacid, and finally forming the diester compound (C) by the reaction with alcohols containing carbon numbers of less than ten in order to effectively carry out the next reduction reaction.

In the above step (d-1), the reduction of the diester compound (C) by lithium aluminum hydride (LAH) produces the diol compound (D). The direct reduction of the diester (C) to the $C_{10}$ dialdehyde, represented by the Chemical Formula 1, is very difficult task because two ester groups should be reduced at the same time to two aldehyde groups, which are more reactive than the starting esters towards the reduction reaction. Considering the effectiveness and the practical applicability of the process, it is more appropriate to reduce the diester (C) all the way to the diol (D), and then to oxidize the diol (D) to the $C_{10}$ dialdehyde of the Chemical Formula 1.

In the above step (e-1), the oxidation of the diol (D) to the $C_{10}$ dialdehyde (Chemical Formula 1) is carried out under various oxidation conditions such as Swern oxidation (DMSO/oxaly chloride/$Et_3N$), $MnO_2$, PCC (pyridinium chlorochromate), and PDC (pyridinium dichromate).

The third technical object of the present invention is achieved by a process for preparing β-carotene of the Chemical Formula 2 which comprises the steps of:

(a-2) deprotonating the $C_{15}$ allylic sulfone compound (E), and then reacting with the $C_{10}$ dialdehyde of the Chemical Formula 1 on the basis of the compound (E) to synthesize the coupling product, the $C_{40}$ diol compound (F);

(b-2) applying the functional group transformation reactions to the above $C_{40}$ diol (F) to produce the corresponding dihalide or diether compound (G); and (c-2) reacting the above protected diol compound (G) with a base to induce the double elimination reactions of the sulfone and the halogen or the ether functional groups producing the conjugated polyene chain (see Scheme 5).

Scheme 5

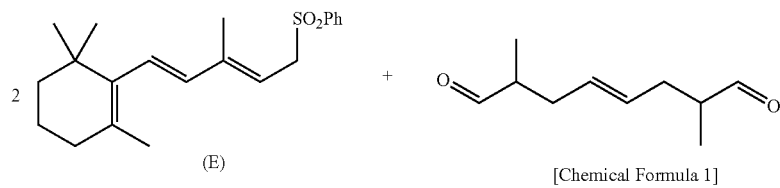

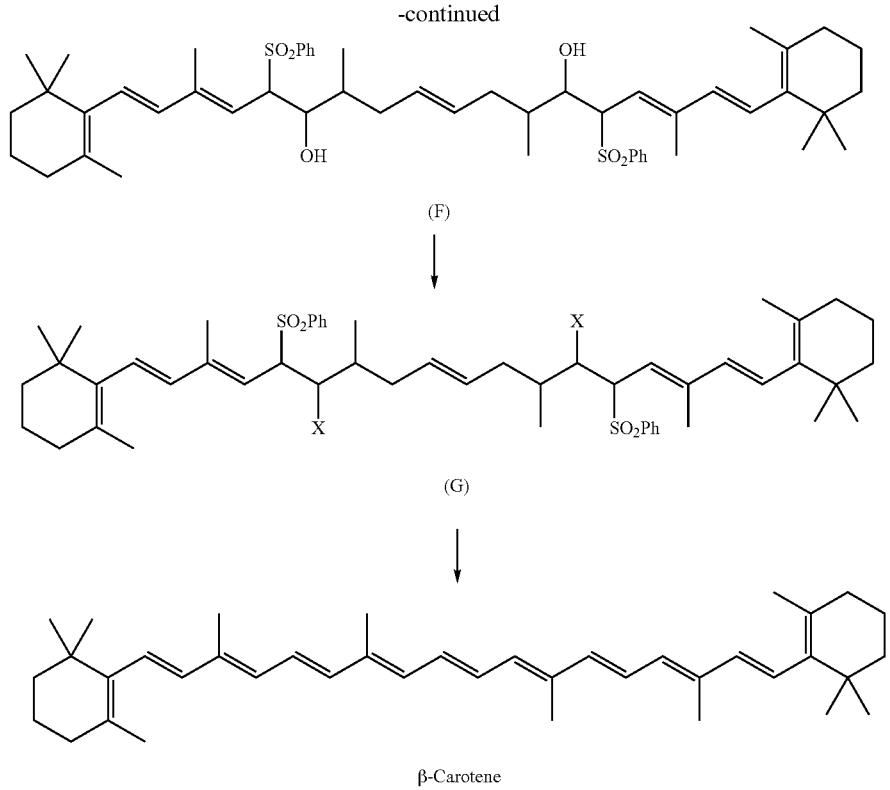

[Chemical Formula 2]

In the formula, X is selected from the group consisting of Cl, Br, THPO (Tetrahydropyranyloxy), EOEO (1-ethoxyethoxy), and MOMO (Methoxymethoxy).

In the above step (a-2), the deprotonation of the $C_{15}$ allylic sulfone (E) is carried out by a strong base such as n-BuLi, s-BuLi, t-BuLi, MeLi, EtMgBr and so on. The coupling reaction of the anion of the $C_{15}$ allylic sulfone (E) with the $C_{10}$ dialdehyde of Chemical Formula 1 can be best carried out at the temperatures below $-20°$ C. It is also necessary to quench the coupling reaction by adding a proton ($H^+$) source at the same temperature to prevent the reverse reaction.

In the above step (b-2), the functional group transformation reactions of the $C_{40}$ diol compound (F) can be carried out by $SOCl_2$ or $PBr_3$ in the presence of pyridine to give the corresponding dichloride or dibromide (G), respectively. On the other hand, transformation of the $C_{40}$ diol (F) to the corresponding THP and EOE ethers (G) can be proceeded by the reaction with 3,4-dihydro-2H-pyran and ethyl vinyl ether, respectively under p-toluenesulfonic acid or 10-camphorsulfonic acid catalyst. The corresponding MOM ether (G) can be efficiently obtained by the reaction with dimethoxymethane in the presence of $P_2O_5$.

In the above step (c-2), the double elimination of the benzenesulfonyl group and the group X, which stands for the halogen (Cl, Br) or the alkoxyalkyloxy group (—OTHP, —OEOE, —OMOM), from the compound (G) can be best carried out using a metal alkoxide base such as MeOK, EtOK, t-BuOK, MeONa, EtONa, and t-BuONa in cyclohexane, hexane, THF, dioxane, benzene, toluene, or xylenes as a solvent at the temperature ranges from $25°$ C. to $150°$ C. to produce the fully conjugated polyene chains. It is desirable to carry out the double elimination reaction at the temperatures higher than $60°$ C. to provide the C═C bonds of (E)-configuration.

ADVANTAGEOUS EFFECTS

The novel $C_{10}$ dialdehyde of the Chemical Formula 1 according to the present invention was devised to be utilized as an important intermediate in the efficient synthesis of the conjugated polyene chains of the carotenoid compounds such as β-carotene by using the sulfone chemistry. The processes of the coupling of the above $C_{10}$ dialdehyde with two equivalents of $C_{15}$ allylic sulfone, the protection of the resulting $C_{40}$ diol, and the double elimination reaction of the protected $C_{40}$ compound efficiently and economically produce β-carotene without going through the Ramberg-Bäcklund reaction, which was the only problematic reaction in the synthesis of β-carotene utilizing the sulfone chemistry. The β-carotene synthesis according to the present invention shows several advantages over the existing methods in the efficiency of the steps, and the handling of the intermediates and the product.

BEST MODES FOR CARRYING OUT THE INVENTION

According to the present invention, the $C_{10}$ dialdehyde of the Chemical Formula 1 is newly devised to efficiently produce the conjugated polyene chain of β-carotene by the double elimination reaction without going through the Ramberg-Bäcklund reaction, and is synthesized in the following process.

The bath temperature of the bromination reaction of 1,3-butadiene (bp $-4.5°$ C.) should be maintained at $-20°$ C. or lower to ensure the effective addition of bromine, where a non-nucleophilic solvent such as $CCl_4$, $CHCl_3$, and $CH_2Cl_2$ etc can be used. This reaction is an electrophilic bromine addition to the conjugated diene, and 1,4- and 1,2-addition products were obtained in a 5:1 ratio, in which pure (E)-1,4-dibromo-2-butene (A) was obtained after recrystallization from hexanes.

Dialkyl methylmalonate including dimethyl methylmalonate, diethyl methylmalonate, or diisopropyl methylmalonate was treated with a base such as NaH, MeONa, EtONa, i-PrONa, t-BuONa, KH, MeOK, EtOK, i-PrOK, and t-BuOK to generate a carbanion. The above carbanion was then reacted with not more than 0.5 equivalent of (E)-1,4-dibromo-2-butene (A) to give 2,7-dialkoxycarbonyl-2,7-dimethyl-4-octenedioic acid, dialkyl ester (B). The alkyl group of dialkyl methylmalonate is selected from the group containing carbon numbers of less than ten. Tetrahydrofuran (THF) or the corresponding alcohol of the metal alkoxide base can be used as a solvent for the above reaction. The temperature of the deprotonation is preferably at 0° C., whilst the coupling reaction is at ambient temperature.

The hydrolysis reaction of 2,7-dialkoxycarbonyl-2,7-dimethyl-4-octenedioic acid, dialkyl ester (B) can be carried out under an alkaline solution of NaOH or KOH at the reflux temperature to hydrolyze all of the four alkyl ester groups. The metal salts of the tetraacid, thus obtained, was treated with concentrated sulfuric acid or nitric acid to adjust the pH of the solution around to 1 to give the corresponding tetraacid, which upon refluxing to the boiling point of the solvent produced 2,7-dimethyl-4-octenedioic acid after decarboxylation reaction.

2,7-Dimethyl-4-octenedial, represented by the Chemical Formula 1, can be obtained by the reduction of 2,7-dimethyl-4-octenedioic acid. Generally, it is not practical to reduce an acid directly to an aldehyde due to low yields of the reaction or the sophisticated reaction conditions requiring an expensive reagent. It is thus preferable to react 2,7-dimethyl-4-octenedioic acid with an alcohol containing carbon numbers of less than ten under an acidic condition to provide the dialkyl ester compound (C), and then to reduce the ester (C) to the aldehyde of the Chemical Formula 1.

Even though the partial reduction method of an ester directly to an aldehyde has been known (Cha, J. S.; Kwon, S. S. *J. Org. Chem.* 1987, 52, 5486-5487), the conversion of the diester (C) to the dialdehyde of the Chemical Formula 1 requires the reduction of the two ester groups at the same time to the more reactive dialdehyde. The alcohol-ester compound is obtained rather than the desired dialdehyde by the reduction of the diester (C) with two equivalent of hydride reducing agent. Therefore, it is preferable to reduce the diester (C) all the way to the diol, and then to oxidize to the dialdehyde of the Chemical Formula 1, considering the effectiveness and practical applicability of the process. 2,7-Dimethyl-4-octenedioic acid, dialkylester (C) was thus reduced by LAH to give 2,7-dimethyl-4-octene-1,8-diol (D), which was then oxidized to 2,7-dimethyl-4-octenedial of the Chemical Formula 1. The oxidation method of the diol (C) to the dialdehyde (D) can be selected from the following lists: Swern oxidation (DMSO/oxalyl chloride/Et$_3$N), MnO$_2$, PCC, and PDC etc.

According to the present invention, β-carotene, represented by the Chemical Formula 2, can be efficiently and economically synthesized by the double elimination method without going through the Ramberg-Bäcklund reaction based on the sulfone chemistry.

The $C_{15}$ allylic sulfone compound (E) (Julia, M.; Arnould, D. *Bull. Soc. Chim. Fr.* 1973, 746-750), which has been efficiently utilized in the synthesis of retinol and β-carotene based on the sulfur chemistry, was deprotonated by a strong base such as n-BuLi, s-BuLi, t-BuLi, MeLi or EtMgBr. The resulting carbanion was then reacted with less than 0.5 equivalent of the above $C_{10}$ dialdehyde of the Chemical Formula 1 to produce the $C_{40}$ diol compound (F) containing the required carbon skeleton for β-carotene. The above coupling reaction should be carried out at the temperatures below −20° C., and quenched by adding a proton (H$^+$) source at the same temperature. The starting $C_{15}$ allylic sulfone (E) can be regenerated from the coupling product (F) by the retro-aldol type reaction at the temperatures higher than −20° C.

The diol of the above $C_{40}$ coupling product (F) can be protected by transforming either to halides or to ethers under acidic conditions. The $C_{40}$ diol (F) reacted with SOCl$_2$ or PBr$_3$ in the presence of pyridine to give the corresponding dichloride or the dibromide (G), respectively. On the other hand, the etherification reactions with 3,4-dihydro-2H-pyran or ethyl vinyl ether in the presence of p-toluenesulfonic acid or 10-camphorsulfonic acid catalysts produced the corresponding THP or EOE ethers (G) of the $C_{40}$ diol (F). The MOM protection of the $C_{40}$ diol (F) can be carried out by the reaction with dimethoxymethane in the presence of P$_2$O$_5$.

Finally, the double elimination reaction, which has been utilized in the synthesis of retinol by Otera (Otera, J.; Misawa, H.; Onishi, T.; Suzuki, S.; Fujita, Y. *J. Org. Chem.* 1986, 51, 3834-3838), was successfully applied for the protected $C_{40}$ compounds (G) to give rise to β-carotene containing the fully conjugated polyene chain. The double elimination reaction can be carried out using a base such as MeOK, EtOK, t-BuOK, MeONa, EtONa, and t-BuONa in the solvent selected from cyclohexane, hexane, THF, dioxane, benzene, toluene, and xylenes at the temperature ranges from 25° C. to 150° C. It is desirable to carry out the reaction at the temperatures higher than 60° C. in order to produce the conjugated polyene chain of (E)-configurations. The double elimination reaction removes the benzenesulfonyl group (PhSO$_2$) and the group X, representing halide or ether functional groups, at the same time to produce the fully conjugated polyene chain of β-carotene.

MODE FOR THE INVENTION

The invention is described in more detail by referring to the examples below, but it should be noticed that those examples are described only to specifically describe the present invention, so that the present invention is not restricted to the examples by any means.

EXAMPLE 1

(E)-1,4-dibromo-2-butene (A)

1,3-Butadiene (60 mL, 0.70 mol) was received in a 500 mL round-bottomed flask which was placed into a −78° C. bath. CCl$_4$ (100 mL), which was already cooled to −20° C., was slowly added to the above flask while maintaining the temperature of the mixture below −20° C. Bromine was then added to the above solution drop wise for 2 h at −20° C. The reaction mixture was stirred vigorously at room temperature for 14 h, and most of the solvent was removed under reduced pressure. The crude product was recrystallized from coldhexanes to give white crystalline 1,4-dibromide (A) (62.4 g, 0.29 mmol) in 58% yield.

$R_f$=0.74 (hexanes:EtOAc=4:1).
$^1$H NMR (300.40 MHz, CDCl$_3$) δ 3.89-4.02 (m, 4H), 5.90-6.05 (m, 2H) ppm.

EXAMPLE 2

2,7-Bis(ethoxycarbonyl)-2,7-dimethyl-4-octenedioic acid, diethyl ester (B).

To a stirred suspension of NaH (8.0 g, 0.20 mol, 60% dispersion in mineral oil) in THF (200 mL) was added a solution of diethyl methylmalonate (17.60 g, 0.10 mol) in THF (10 mL) at 0° C. The mixture was stirred at that temperature for 30 min, and a solution of (E)-1,4-dibromo-2-butene (A) (10.70 g, 50.0 mmol) in THF (10 mL) was added. The reaction mixture was slowly warmed to and stirred at room temperature for 14 h, and 1 M HCl solution was added. The mixture was extracted with Et$_2$O, washed with H$_2$O and brine, dried over Na$_2$SO$_4$, filtered, and concentrated under reduced pressure. The crude product was purified by SiO$_2$ flash column chromatography (hexanes:EtOAc=10:1) to give the tetraester (B) (17.6 g, 44.0 mmol) in 88% yield
$R_f$=0.58 (hexanes:EtOAc=4:1).
$^1$H NMR (300.40 MHz, CDCl$_3$) δ 1.24 (t, J=7.2 Hz, 12H), 1.35 (s, 6H), 2.49-2.62 (m, 4H), 4.17 (q, J=7.2 Hz, 8H), 5.33-5.48 (m, 2H) ppm.
HRMS (CI, H$^+$) calcd for C$_{20}$H$_{33}$O$_8$ 401.2175, found 401.2170.

EXAMPLE 3

2,7-Dimethyl-4-octenedioic acid, dimethyl ester (C)

The mixture of the tetraester compound (B) (9.4 g, 23.5 mmol) and KOH (26.4 g, 47.0 mmol) in H$_2$O (200 mL) was heated to reflux for 2 d. The reaction mixture was cooled to room temperature, and acidified to pH 1 by adding concentrated H$_2$SO$_4$. The resulting mixture was heated to reflux for 3 d, and then cooled to room temperature. The mixture was extracted with EtOAc, dried over Na$_2$SO$_4$, filtered, and concentrated under reduced pressure. The crude product (5.8 g) was dissolved in MeOH (80 mL), and treated with concentrated H$_2$SO$_4$ (3.5 mL). The mixture was then stirred at room temperature for 12 h. Most of the solvent was removed under reduced pressure. The concentrate was dissolved in EtOAc, washed with H$_2$O, dried over Na$_2$SO$_4$, filtered, and concentrated under reduced pressure. The crude product was purified by SiO$_2$ flash column chromatography (hexanes:EtOAc=4:1) to give the dimethyl ester (C) (4.75 g, 20.9 mmol) in 89% yield.
$R_f$=0.50 (hexanes:EtOAc=4:1)
$^1$H NMR (300.40 MHz, CDCl$_3$) δ 1.13 (d, J=7.0 Hz, 6H), 2.05-2.20 (m, 2H), 2.26-2.40 (m, 2H), 2.48 (tq, J$_t$=7.0, J$_q$=7.0 Hz, 2H), 3.66 (s, 6H), 5.31-5.48 (m, 2H) ppm.
HRMS (CI, H$^+$) calcd for C$_{12}$H$_{21}$O$_4$ 229.1440, found 229.1443.

EXAMPLE 4

2,7-Dimethyl-4-octene-1,8-diol (D)

To a stirred suspension of LiAlH$_4$ (1.64 g, 41.0 mmol) in THF (65 mL) was added a solution of the dimethyl ester (C) (4.67 g, 20.5 mmol) in THF (15 mL) at 0° C. The mixture was stirred at that temperature for 30 min, and warmed up and stirred at room temperature for 1 h. The reaction mixture was quenched with 5% NaOH solution, extracted with Et$_2$O thoroughly, dried over Na$_2$SO$_4$, filtered, and concentrated under reduced pressure. The crude product was purified by SiO$_2$ flash column chromatography (hexanes:EtOAc=2:1) to give the diol (D) (3.53 g, 20.5 mmol) in 100% yield.
$R_f$=0.33 (hexanes:EtOAc=1:1).
$^1$H NMR (300.40 MHz, CDCl$_3$) δ 0.91 (d, J=6.8 Hz, 6H), 1.69 (ttq, J$_t$=6.5, 6.6, J$_q$=6.4 Hz, 2H), 1.85-1.97 (m, 2H), 1.93 (s, 2H), 2.05-2.17 (m, 2H), 3.48 (d of A of ABq, J$_{AB}$=10.5, J$_d$=6.0 Hz, 2H), 3.50 (d of B of ABq, J$_{AB}$=10.5, J$_d$=6.1 Hz, 2H), 5.37-5.52 (m, 2H) ppm.
HRMS (CI, H$^+$) calcd for C$_{10}$H$_{21}$O$_2$ 173.1541, found 173.1541.

EXAMPLE 5

2,7-Dimethyl-4-octenedial (Chemical Formula 1)

To a stirred solution of DMSO (0.722 g, 9.24 mmol) in CH$_2$Cl$_2$ (10 mL) was added oxalyl chloride (0.40 mL, 4.62 mmol) at −78° C. The mixture was stirred for 5 min, and a solution of the diol (D) (0.362 g, 2.1 mmol) in CH$_2$Cl$_2$ (3 mL) was added. The resulting mixture was stirred at −78° C. for 15 min, and Et$_3$N (2.93 mL, 21 mmol) was added. Stirring for 5 min at that temperature, the mixture was then warmed up to room temperature, and quenched with 1 M HCl solution. The mixture was diluted with CH$_2$Cl$_2$, washed with H$_2$O, dried over Na$_2$SO$_4$, filtered, and concentrated under reduced pressure. The crude product was purified by SiO$_2$ flash column chromatography (hexanes:EtOAc=5:1) to give the dialdehyde of the Chemical Formula 1 (0.307 g, 1.824 mmol) in 87% yield.
$R_f$=0.86 (hexanes:EtOAc=1:1).
$^1$H NMR (300.40 MHz, CDCl$_3$) δ 1.09 (d, J=6.6 Hz, 6H), 2.05-2.20 (m, 2H), 2.34-2.50 (m, 4H), 5.38-5.53 (m, 2H), 9.64 (d, J=1.3 Hz, 2H) ppm
HRMS (CI, H$^+$) calcd for C$_{10}$H$_{17}$O$_2$ 169.1228. found 169.1226.

EXAMPLE 6

5,14-Bis(benzenesulfonyl)-3,7,12,16-tetramethyl-1, 18-bis(2,6,6-trimethyl-1-cyclohexenyl)octadeca-1,3, 9,15,17-pentaene-6,13-diol (F)

To a stirred solution of 1-benzenesulfonyl-3-methyl-5-(2, 6,6-trimethyl-1-cyclohexenyl)-2,4-pentadiene (E) (3.09 g, 8.97 mmol) in THF (40 mL) was added 1.6 M solution of n-BuLi in hexane (6.6 mL, 10.61 mmol) at −78° C. The mixture was stirred at that temperature for 20 min, and a solution of 2,7-dimethyl-4-octenedial of the Chemical Formula 1 (686 mg, 4.08 mmol) in THF (10 mL) was added. The resulting mixture was stirred at −78° C. for 1 h, and quenched with 1 M HCl solution (20 mL). The mixture was diluted with ether, washed with 1 M HCl solution, dried over Na$_2$SO$_4$, filtered, and concentrated under reduced pressure. The crude product was purified by SiO$_2$ flash column chromatography (hexanes:EtOAc=4:1~3:2) to give the C$_{40}$ diol (F) (3.35 g, 3.91 mmol) in 96% yield as a white solid, which contained many stereoisomers due to the presence of six chiral centers. The major stereoisomer, which was presumed to be all-(E)-isomer, was carefully purified again by preparative TLC for spectroscopic analysis.
$R_f$=0.15~0.23 (hexanes:EtOAc=4:1).
$^1$H NMR (300.40 MHz, CDCl$_3$, major) δ 0.75 (d, J=6.8 Hz, 6H), 0.96 (s, 6H), 0.99 (s, 6H), 1.22 (s, 6H), 1.40-1.50 (m, 4H), 1.50-1.70 (m, 6H), 1.67 (s, 6H), 1.90-2.25 (m, 8H), 2.65 (br s, 2H), 4.04 (dd, J=11.0, 9.3 Hz, 2H), 4.37 (dd, J=9.2, 1.8 Hz, 2H), 4.98 (d, J=11.0 Hz, 2H), 5.32-5.50 (m, 2H), 5.96 (s, 4H), 7.44-7.55 (m, 4H), 7.58-7.68 (m, 2H), 7.75-7.85 (m, 4H) ppm.

EXAMPLE 7

5,14-Bis(benzenesulfonyl)-6,13-dibromo-3,7,12,16-tetramethyl-1,18-bis(2,6,6-trimethyl-1-cyclohexenyl)(octadeca-1,3,9,15,17-pentaene (G-1).

To a stirred solution of the $C_{40}$ diol (F) (1.00 g, 1.17 mmol) in $CH_2Cl_2$ were added pyridine (0.47 mL, 5.85 mmol) and $PBr_3$ (0.11 mL, 1.17 mmol) at 0° C. The mixture was then stirred at room temperature for 1 h, diluted with $CH_2Cl_2$, washed with 1 M HCl solution, dried over $Na_2SO_4$, filtered, and concentrated under reduced pressure to give the $C_{40}$ dibromide (G-1) (1.10 g, 1.12 mmol) in 96% crude yield as a shiny yellow solid. The peaks of the $^1H$ NMR spectrum of (G-1) were so broad that those were not able to be assigned.

HRMS (FAB$^+$) Calcd for $C_{46}H_{66}BrO_2S$ ($C_{52}H_{72}Br_2O_4S_2$—$C_6H_6O_2S$—Br) 761.3967, found 761.3952.

EXAMPLE 8

5,14-Bis(benzenesulfonyl)-3,7,12,16-tetramethyl-1,18-bis(2,6,6-trimethyl-1-cyclohexenyl)octadeca-1,3,9,15,17-pentaene-6,13-diol, bis(tetrahydropyranyl)ether (G-2)

To a stirred solution of the $C_{40}$ diol (F) (1.59 g, 1.85 mmol) in $CH_2Cl_2$ (35 mL) were added 3,4-dihydro-2H-pyran (1.01 mL, 11.11 mmol) and 10-camphorsulfonic acid (129 mg, 0.56 mmol). The mixture was stirred at room temperature for 14.5 h, diluted with $CH_2Cl_2$, washed with 10% $NaHCO_3$ solution, dried over $Na_2SO_4$, filtered, and concentrated under reduced pressure. The crude product (2.75 g) was purified by $SiO_2$ flash column chromatography (hexanes:EtOAc=9:1~7:3) to give the $C_{40}$ THP diether (G-2) (1.65 g, 1.61 mmol) in 87% yield as a light yellow solid, which contained many stereoisomers due to the presence of eight chiral centers. The major stereoisomer, which was presumed to be all-(E)-isomer, was carefully purified again by preparative TLC for spectroscopic analysis.

$R_f$=0.20~0.25 (hexanes:EtOAc=4:1).

$^1H$ NMR (300.40 MHz, CDCl$_3$, major) δ 0.96 (s, 12H), 0.99 (s, 6H), 1.23 (s, 6H), 1.40-1.94 (m, 20H), 1.66 (s, 6H), 1.94-2.05 (m, 8H), 2.47 (t, J=7.2 Hz, 2H), 3.40 (dt, $J_d$=9.7, $J_t$=6.1 Hz, 2H), 3.76 (dt, $J_d$=9.7, $J_t$=6.3 Hz, 2H), 4.04 (dd, J=10.8, 9.4 Hz, 2H), 4.36 (dd, J=9.1, 1.8 Hz, 2H), 4.57 (dd, J=4.2, 2.9 Hz, 2H), 4.97 (d, J=11.2 Hz, 2H), 5.41 (t, J=4.1 Hz, 2H), 5.96 (s, 4H), 7.35-7.60 (m, 4H), 7.60-7.70 (m, 2H), 7.75-7.85 (m, 4H) ppm.

EXAMPLE 9

5,14-Bis(benzenesulfonyl)-3,7,12,16-tetramethyl-1,18-bis(2,6,6-trimethyl-1-cyclohexenyl)octadeca-1,3,9,15,17-pentaene-6,13-diol, bis(1-ethoxyethyl)ether (G-3)

To a stirred solution of the $C_{40}$ diol (F) (0.634 g, 0.74 mmol) in $CH_2Cl_2$ (7 mL) were added pyridinium p-toluenesulfonate (0.075 g, 0.30 mmol) and ethyl vinyl ether (0.43 mL, 4.44 mmol) at 0° C. After stirring for 2 h at that temperature, it was warmed and stirred at room temperature overnight. The mixture was diluted with $CH_2Cl_2$ and 10% $NaHCO_3$ solution was added. The organic layer was separated, washed with $H_2O$, dried over $Na_2SO_4$, filtered, and concentrated under reduced pressure. The crude product (0.75 g) was purified by $SiO_2$ flash column chromatography (hexanes:EtOAc=6:1~4:1) to give the $C_{40}$ 1-ethoxyethyl diether (G-3) (0.674 g, 0.673 mmol) in 91% yield as a white solid, which contained many stereoisomers due to the presence of eight chiral centers.

$R_f$=0.20~0.40 (hexanes:EtOAc=4:1).

EXAMPLE 10

5,14-Bis(benzenesulfonyl)-3,7,12,16-tetramethyl-1,18-bis(2,6,6-trimethyl-1-cyclohexenyl)octadeca-1,3,9,15,17-pentaene-6,13-diol, bis(methoxymethyl)ether (G-4)

To a stirred solution of the $C_{40}$ diol (F) (1.183 g, 1.38 mmol) in dimethoxymethane (2.45 mL, 27.6 mmol) was added $P_2O_5$ (0.12 g, 0.83 mmol) at room temperature. After stirring 5 h, additional portion of $P_2O_5$ (0.12 g, 0.83 mmol) was added again to the mixture. After stirring for 20 h at room temperature, the mixture was extracted with toluene and 10% $NaHCO_3$ solution was added. The organic layer was washed again with 10% $NaHCO_3$ solution, dried over $Na_2SO_4$, filtered, and concentrated under reduced pressure. The crude product (1.42 g) was purified by $SiO_2$ flash column chromatography (hexanes:EtOAc=8:1~2:1) to give the $C_{40}$ MOM diether (G-4) (1.212 g, 1.282 mmol) in 93% yield as a white solid, which contained many stereoisomers due to the presence of six chiral centers. The major stereoisomer, which was presumed to be all-(E)-isomer, was carefully purified again by preparative TLC for spectroscopic analysis $R_f$=0.17~0.25 (hexanes:EtOAc=4:1).

$^1H$ NMR (300.40 MHz, CDCl$_3$, major) δ 0.93 (s, 6H), 0.95 (s, 6H), 0.98 (d, J=5.9 Hz, 6H), 1.16 (s, 6H), 1.35-1.50 (m, 4H), 1.50-1.70 (m, 6H), 1.62 (s, 6H), 1.70-1.87 (m, 2H), 1.92-2.13 (m, 6H), 3.41 (s, 6H), 4.16 (d, J=7.7 Hz, 2H), 4.29 (dd, J=11.4, 7.7 Hz, 2H), 4.77 (d, J=7.2 Hz, 2H), 4.94 (d, J=7.2 Hz, 2H), 5.16 (d, J=11.4 Hz, 2H), 5.20 (br s, 2H), 5.88 (s, 4H), 7.38-7.48 (m, 4H), 7.50-7.60 (m, 2H), 7.72-7.84 (m, 4H) ppm.

EXAMPLE 11

β-carotene (Chemical Formula 2)

Method A. To a stirred suspension of the crude $C_{40}$ dibromide (G-1) (1.34 g, 1.36 mmol) in cyclohexane (40 mL) was added KOMe (2.00 g, 28.48 mmol). The mixture was heated to 60° C.~80° C. for 8.5 h, and cooled to room temperature. The mixture was then diluted with hexanes/benzene, washed with $H_2O$ and 1 M HCl solution, dried over $Na_2SO_4$, filtered, and concentrated under reduced pressure to give a dark-red solid (779 mg). The crude product was purified by dissolving in hexanes (60 mL) and washing with MeCN (30 mL×3). The MeCN layer was extracted again with hexanes, and the combined hexanes layer was concentrated under reduced pressure to give β-carotene (584 mg, 1.09 mmol) in 80% yield as a red solid, which was consisted of a 4:1 mixture of all-(E) and 13-(Z) stereoisomers. The product was further purified by $SiO_2$ flash column chromatography to give all-(E)-β-carotene in 38% yield Method B. To a stirred solution of the $C_{40}$ THP diether (G-2) (1.50 g, 1.46 mmol) in cyclohexane (50 mL) was added KOMe (2.05 g, 29.25 mmol). The mixture was heated to 50° C.~60° C. for 6 h, and cooled to room temperature. The mixture was then diluted with hexanes/benzene, washed with 1 M HCl solution, dried over $Na_2SO_4$, filtered, and concentrated under reduced pressure. The crude product (1.26 g), which was consisted of a 4:1 mixture of all-(E) and 13-(Z) stereoisomers, was purified by $SiO_2$ flash column chromatography (hexanes:EtOAc=32:1) to give all-(E)-β-carotene (228 mg, 0.42 mmol) in 29% yield as a red solid.

Method C. To a stirred solution of the $C_{40}$ 1-ethoxyethyl diether (G-3) (0.6 g, 0.6 mmol) in cyclohexane (20 mL) was added KOMe (0.842 g, 12.0 mmol). The mixture was heated to 80° C. for 16 h, and cooled to room temperature. The mixture was then diluted with hexanes, washed 3 times with $H_2O$, dried over $Na_2SO_4$, filtered, and concentrated under reduced pressure. The crude product (0.317 g), which was consisted of a 4:1 mixture of all-(E) and 13-(Z) stereoisomers, was purified by recrystallization (THF:MeOH=1:5) to give all-(E)-β-carotene (0.226 g, 0.42 mmol) in 70% yield as a red solid.

Method D. To a stirred solution of the $C_{40}$ MOM diether (G-4) (0.945 g, 1.0 mmol) in cyclohexane (25 mL) was added KOMe (1.403 g, 20.0 mmol). The mixture was heated to 80° C. for 16 h, and cooled to room temperature. The mixture was then diluted with hexanes, washed 3 times with $H_2O$, dried over $Na_2SO_4$, filtered, and concentrated under reduced pressure. The crude product (0.548 g), which was consisted of a 4:1 mixture of all-(E) and 13-(Z) stereoisomers, was purified by recrystallization (THF:MeOH=1:5) to give all-(E)-β-carotene (0.453 g, 0.84 mmol) in 84% yield as a red solid.

The $^1$H NMR data of all-(E)-β-carotene was identical with those of the authentic sample.

INDUSTRIAL APPLICABILITY

The carotenoid compounds are biologically, medicinally, and industrially important natural products. β-Carotene, the most representative carotenoid, has been widely utilized as an animal feed, a food additive for human, and a colorant. β-Carotene has been also utilized as a nutraceutical due to its vitamin A activity in cell growth and proliferation. Furthermore, a prophylaxis effect on certain cancers has made β-carotene as one of the most valuable cancer preventive agent. The present invention provides highly efficient and practical synthetic method of β-carotene, which makes use of the stable sulfone intermediates and the double elimination strategy to effectively build the conjugated polyene chain within several steps.

The invention claimed is:

1. 2,7-dimethyl-4-octenedial represented by the Chemical Formula 1

[Chemical Formula 1]

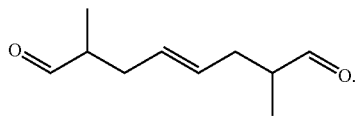

2. A process for preparing $C_{10}$ dialdehyde which comprises the steps of:
   (a-1) reacting 1,3-butadiene with bromine to give (E)-1,4-dibromo-2-butene (A);
   (b-1) reacting the above compound (A) with dialkyl methylmalonate to produce 2,7-dialkoxycarbonyl-2,7-dimethyl-4-octenedioic acid, dialkyl ester (B);
   (c-1) hydrolyzing the above tetraester (B) to produce tetraacid, followed by decarboxylating the tetraacid to give the diacid, and then reacting the diacid with alcohols containing carbon numbers of less than ten to provide 2,7-dimethyl-4-octenedioic acid, dialkyl ester (C);
   (d-1) reducing the diester (C) to give 2,7-dimethyl-4-octene-1,8-diol (D); and
   (e-1) oxidizing the above diol (D) to 2,7-dimethyl-4-octenedial, represented by the Chemical Formula 1,

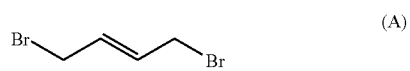

(A)

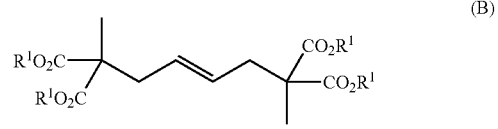

(B)

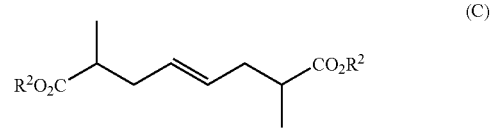

(C)

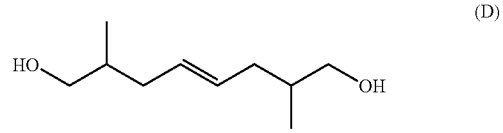

(D)

[Chemical Formula 1]

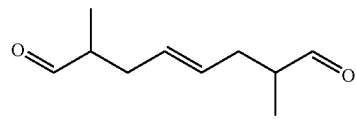

wherein $R^1$ and $R^2$ are independently selected from the alkyl groups containing carbon numbers of less than ten.

3. A process for preparing β-carotene of the Chemical Formula 2 which comprises the steps of:
   (a-2) deprotonating the $C_{15}$ allylic sulfone compound (E), and then reacting with $C_{10}$ dialdehyde of the Chemical Formula 1 to produce the $C_{40}$ diol compound (F);
   (b-2) applying the functional group transformation reactions to the above $C_{40}$ diol (F) to produce the corresponding dihalide or diether compound (G); and
   (c-2) reacting the above protected diol compound (G) with a base to induce the double elimination reactions producing the conjugated polyene chain,

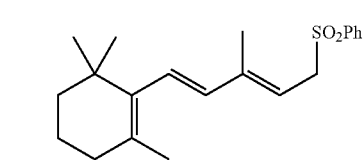
(E)

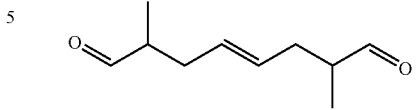
[Chemical Formula 1]

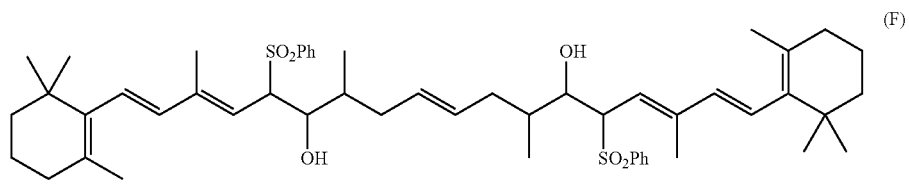
(F)

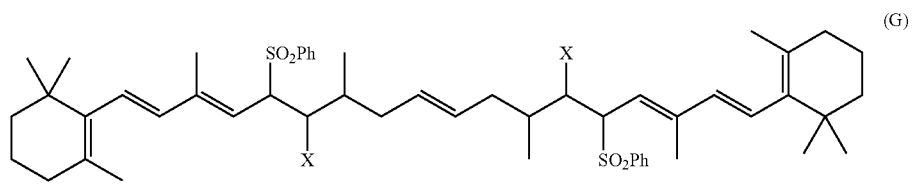
(G)

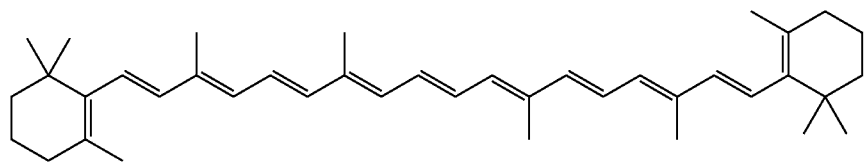
[Chemical Formula 2]

wherein X is selected from the group consisting of Cl, Br, THPO (Tetrahydropyranyloxy), EOEO (1-ethoxyethoxy), and MOMO (Methoxymethoxy).

4. A process for preparing β-carotene according to claim 3, wherein the deprotonation of the $C_{15}$ allylic sulfone (E) in step (a-2) is carried out by a base selected from the group consisting of n-BuLi, s-BuLi, t-BuLi, MeLi, and EtMgBr.

5. A process for preparing β-carotene according to claim 3, wherein the coupling reaction with the $C_{10}$ dialdehyde of the Chemical Formula 1 in step (a-2) is carried out at the temperatures below −20° C., and quenched at the same temperature by adding a proton ($H^+$) source to the mixture.

6. A process for preparing β-carotene according to claim 3, wherein the functional group transformation reaction of the $C_{40}$ diol (F) in step (b-2) is carried out by reacting with $SOCl_2$ or $PBr_3$ to produce the corresponding chloride or the bromide compound (G).

7. A process for preparing β-carotene according to claim 3, wherein the functional group transformation reaction of the $C_{40}$ diol (F) in step (b-2) is carried out by reacting 3,4-dihydro-2H-pyran or ethyl vinyl ether in the presence of p-toluenesulfonic acid or 10-camphorsulfonic acid catalyst or reacting dimethoxymethane in the presence of $P_2O_5$ to produce the corresponding ether compound (G).

8. A process for preparing β-carotene according to claim 3, wherein the double elimination reaction of the protected $C_{40}$ compound (G) in step (c-2) is carried out by using a metal alkoxide base such as MeOK, EtOK, t-BuOK, MeONa, EtONa, and t-BuONa in the solvent selected from cyclohexane, hexanes, THF, dioxane, benzene, toluene, and xylenes at the temperatures between 25° C. to 150° C.

* * * * *